(12) United States Patent
Garalde et al.

(10) Patent No.: US 12,042,790 B2
(45) Date of Patent: Jul. 23, 2024

(54) APPARATUS AND METHODS FOR CONTROLLING INSERTION OF A MEMBRANE CHANNEL INTO A MEMBRANE

(71) Applicant: Oxford Nanopore Technologies PLC, Oxford (GB)

(72) Inventors: Daniel Ryan Garalde, Cambridge, MA (US); James Anthony Clarke, Oxford (GB); Mike Jennison, Oxford (GB); Andrew John Heron, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 1360 days.

(21) Appl. No.: 16/463,617

(22) PCT Filed: Nov. 24, 2017

(86) PCT No.: PCT/GB2017/053538
§ 371 (c)(1),
(2) Date: May 23, 2019

(87) PCT Pub. No.: WO2018/096348
PCT Pub. Date: May 31, 2018

(65) Prior Publication Data
US 2020/0179920 A1 Jun. 11, 2020

(30) Foreign Application Priority Data
Nov. 24, 2016 (GB) ...................................... 1619930

(51) Int. Cl.
*B01L 3/00* (2006.01)
*B81C 1/00* (2006.01)

(52) U.S. Cl.
CPC .......... *B01L 3/502* (2013.01); *B81C 1/00071* (2013.01); *B01L 2300/044* (2013.01); *B01L 2400/0415* (2013.01)

(58) Field of Classification Search
CPC ............... B01L 3/502; B01L 2300/044; B01L 2400/0415; B81C 1/00071
See application file for complete search history.

(56) References Cited

U.S. PATENT DOCUMENTS 6,723,814 B2 4/2004 Meier et al.
2012/0052188 A1 3/2012 Chen et al.
(Continued)

FOREIGN PATENT DOCUMENTS

JP H07-320752 A 12/1995
JP 2012-026986 A 2/2012
(Continued)

OTHER PUBLICATIONS

International Search Report and Written Opinion for Application No. PCT/GB2017/053538, dated Feb. 7, 2018.
(Continued)

*Primary Examiner* — Mathieu D Vargot
(74) *Attorney, Agent, or Firm* — Wolf, Greenfield & Sacks, P.C.

(57) ABSTRACT

Apparatus and methods for controlling the insertion of a membrane channel into a membrane are disclosed. In one arrangement a first bath holds a first liquid in contact with a first surface of a membrane. A second bath holds a second liquid in contact with a second surface of the membrane. The membrane separates the first and second liquids. A first electrode contacts the first liquid. A second electrode contacts the second liquid. A driving unit applies a potential difference across the membrane via the first and second electrodes to promote insertion of a membrane channel into (Continued)

the membrane from the first liquid or the second liquid. A membrane voltage reduction unit is connected in series with the membrane. The driving unit applies a driving voltage across the membrane voltage reduction unit and the membrane, the driving voltage providing the potential difference across the membrane. The membrane voltage reduction unit is configured such that a reduction in resistance through the membrane caused by insertion of a membrane channel intrinsically increases a potential difference across the membrane voltage reduction unit thereby lowering the potential difference across the membrane. The lowering of the potential difference across the membrane is sufficient to prevent or reduce promotion of insertion of a further membrane channel.

18 Claims, 5 Drawing Sheets

(56) References Cited

U.S. PATENT DOCUMENTS

| | | | |
|---|---|---|---|
| 2014/0262820 | A1 | 9/2014 | Kuan et al. |
| 2015/0259724 | A1 | 9/2015 | Guan et al. |
| 2016/0289758 | A1 | 10/2016 | Akeson et al. |

FOREIGN PATENT DOCUMENTS

| | | | |
|---|---|---|---|
| JP | 2015-051013 A | | 3/2015 |
| JP | 2015-517799 A | | 6/2015 |
| JP | 2016-095314 A | | 5/2016 |
| WO | WO 2000/079257 A1 | | 12/2000 |
| WO | WO 2001/042782 A1 | | 6/2001 |
| WO | WO 2007/057668 A1 | | 5/2007 |
| WO | WO 2008/012552 A1 | | 1/2008 |
| WO | WO 2008/102120 A1 | | 8/2008 |
| WO | WO 2009/035647 A1 | | 3/2009 |
| WO | WO 2011/097028 A1 | | 8/2011 |
| WO | WO 2013/041878 A1 | | 3/2013 |
| WO | WO 2013/057495 A2 | | 4/2013 |
| WO | WO 2013/098561 A1 | | 7/2013 |
| WO | WO 2013/098562 A2 | | 7/2013 |
| WO | WO 2013/121224 A1 | | 8/2013 |
| WO | WO 2013/123379 A2 | | 8/2013 |
| WO | WO 2013/153359 A1 | | 10/2013 |
| WO | WO 2014/064443 A2 | | 5/2014 |
| WO | WO 2014/064444 A1 | | 5/2014 |
| WO | WO 2016/034591 A2 | | 3/2016 |
| WO | WO 2016/099673 A1 | | 6/2016 |
| WO | WO 2016/142925 A1 | | 9/2016 |
| WO | WO 2016/181465 A1 | | 11/2016 |

OTHER PUBLICATIONS

International Preliminary Report on Patentability for Application No. PCT/GB2017/053538, dated Jun. 6, 2019.

Renner et al., Voltage-controlled insertion of single alpha-hemolysin and *Mycobacterium smegmatis* nanopores into lipid bilayer membranes. Applied Physics Letters, A I P Publishing Llc. Feb. 23, 2011;98(8):83701.

United Kingdom Search Report for Application No. GB1619930.9, mailed Aug. 21, 2017.

Gonzalez-Perez et al., Biomimetic triblock copolymer membrane arrays: a stable template for functional membrane proteins. Langmuir. Sep. 15, 2009;25(18):10447-50. doi: 10.1021/la902417m.

Heron et al., Simultaneous measurement of ionic current and fluorescence from single protein pores. J Am Chem Soc. Feb. 11, 2009;131(5):1652-3. doi: 10.1021/ja808128s.

Langecker et al., Synthetic lipid membrane channels formed by designed DNA nanostructures. Science. Nov. 16, 2012;338(6109):932-6. doi: 10.1126/science.1225624.

Montal et al., Formation of bimolecular membranes from lipid monolayers and a study of their electrical properties. Proc Natl Acad Sci U S A. Dec. 1972;69(12):3561-6. doi: 10.1073/pnas.69.12.3561.

APPARATUS AND METHODS FOR CONTROLLING INSERTION OF A MEMBRANE CHANNEL INTO A MEMBRANE

RELATED APPLICATIONS

This Application is a national stage filing under 35 U.S.C. 371 of international application number PCT/GB2017/053538, filed Nov. 24, 2017, which claims the benefit of United Kingdom application number 1619930.9, filed Nov. 24, 2016, each of which is herein incorporated by reference in its entirety.

FIELD OF THE INVENTION

The invention relates to apparatus and methods for controlling the insertion of a membrane channel into a membrane.

BACKGROUND

Channels formed across membranes can be used to sense molecular entities. Interactions between the molecular entities and the channel can cause characteristic modulations of a signal. By monitoring this signal it is possible to detect the characteristic modulations and thereby sense the molecular entities. A variety of technologies have been proposed based on this principle, such as disclosed in WO2008102120, WO2009035647, WO200079257, WO200142782 and WO2007057668. An example of such is the measurement of a current signal due to the flow of ions through a membrane channel. The membrane separates two solutions wherein the membrane channel provides a transport path through the membrane between the solutions. The membrane is highly resistive such that the sole transport pathway between the solutions is through the membrane channel or channels. The molecular entity of interest may be caused to interact with the channel, for example caused to translocate the channel.

Sensing of molecular entities using this technique provides a method of identifying single molecules and molecular entities directly, without the need for fluorescent labelling and detection. There are a wide range of possible applications, such as sequencing of DNA or other nucleic acids; sensing of chemical or biological molecules for security and defence; detection of biological markers for diagnostics; ion channel screening for drug development; and label free analysis of interactions between biological molecules.

To provide adequate throughput, an array of individual membranes may be provided wherein each membrane comprises a membrane channel.

The membrane is typically amphiphilic and may be a bilayer. Techniques for forming amphiphilic layers are well-known, such as disclosed by Montal and Mueller Proc Natl Acad Sci USA. 1972 December; 69(12): 3561-3566, WO-2008/102120, WO2008012552 and WO2014064444. The thickness of the resultant membrane may vary due to factors such as the nature of the membrane material, solvent incorporation, the membrane geometry as well as the method of preparation.

For some systems, in the absence of an additional stimulus, membrane channels do not spontaneously insert into membranes and often insert very slowly. Selecting such a system can be advantageous as it allows control over the process of membrane insertion. Techniques to assist with insertion of membrane channels are known, the most common being the application of a potential difference across the membrane. It is thought that this potential difference stretches and thins the membrane facilitating easier insertion. Voltage assisted insertion may also be used to control the number of membrane channels that are inserted into a membrane wherein the applied potential may be actively lowered in response to membrane channel insertion and the corresponding detection of current flow through the membrane, wherein lowering of the applied potential difference following insertion of a membrane channel lowers the probability of insertion of a subsequent channel Lowering of the applied potential may be carried out by the user which is common practise for many laboratories forming membranes and making single channel recordings. The downside to this approach is that is requires the user to observe the current of the channel (or similar observable parameter, such as resistance) and to manually react to a change in that parameter. While this is practical for single channel recordings it is impractical when dealing with a large array. It is therefore desirable to automate this process.

Various methods have been disclosed that automate the control of applied potential for an array of membranes. One uses computer control to react to the detection of an increase in the observed current flow as a consequence of nanopore insertion as disclosed by US20160289758. Another method teaches the use of an electrode mediated gas bubble to aid in membrane formation and an agitation stimulus, to achieve a similar affect, as disclosed by US20120052188. The number of channels that are required for each membrane may vary depending upon the measurement technique used. For ion flow measurements it is desirable to provide one channel per membrane.

SUMMARY OF THE INVENTION

While the use of computer controlled automation of a stimulus, such as applied potential, is beneficial over the more manual methods of controlled pore insertion, they have a number of features that are undesirable. One such feature is the need for a computer, or similar decision making circuit, to perform the operation of removing or reducing the pore insertion stimulus. Such circuits are expensive and may not be practical when dealing with a large array of membranes. Each membrane must be subject to this process of computer control to ensure good single channel yield and must either be connected to a dedicated computer control unit or must share a computer control unit between other membranes. Providing a dedicated computer control unit per channel is expensive. While connecting multiple membranes to a control unit reduces this cost that the consequence is that pore insertion is carried out in a consecutive fashion as the control unit cycles around each membrane in turn. This can increase the overall amount of time for required for pore insertion across the array (selection multiplexing), or reduce the reaction time of the device (time shared multiplexing). Furthermore insertion of channels in a consecutive fashion by addition of protein nanopores to a solution in contact with the membrane has been found to result in adsorption of the nanopores to the walls of the vessel due to the increased time that the nanopores are in solution prior to being inserted. This can reduce the yield of inserted nanopores across the array.

An approach which overcomes the problems as detailed above and which is set out in aspects of the invention is to employ a circuit element which intrinsically reduces the applied potential across the membrane when a channel inserts. In some embodiments, this does not require decision making electronics and can be deployed cheaply across a large array. The circuit comprises a membrane voltage reduction unit which redistributes the applied potential across the circuit such that the potential difference across the membrane is lowered following insertion of a membrane channel. The redistribution effect happens automatically, without the need for logic control.

According to an aspect of the invention, there is provided an apparatus for controlling insertion of a membrane channel into a membrane, comprising:
  a first bath for holding a first liquid in contact with a first surface of the membrane;
  a second bath for holding a second liquid in contact with a second surface of the membrane, wherein the membrane separates the first and second liquids;
  a first electrode configured to contact the first liquid;
a second electrode configured to contact the second liquid; and
a driving unit configured to apply a potential difference across the membrane via the first and second electrodes to promote insertion of a membrane channel into the membrane from the first liquid or the second liquid, wherein:
the apparatus comprises a membrane voltage reduction unit connected in series with the membrane; the driving unit is configured to apply a driving voltage across the membrane voltage reduction unit and the membrane, the driving voltage providing the potential difference across the membrane; and
the membrane voltage reduction unit is configured such that a reduction in resistance through the membrane caused by insertion of a membrane channel intrinsically increases a potential difference across the membrane voltage reduction unit thereby lowering the potential difference across the membrane, wherein the lowering of the potential difference across the membrane is sufficient to prevent or reduce promotion of insertion of a further membrane channel The channel may be a nanopore. The nanopore may be a protein channel.

In a further aspect, there is provided an apparatus for inserting a membrane protein into a membrane to form a channel in the membrane, comprising:
  a first bath for holding a first liquid in contact with a first surface of the membrane;
  a second bath for holding a second liquid in contact with a second surface of the membrane wherein the membrane separates the first and second liquids;
  a first electrode configured to contact the first liquid;
a second electrode configured to contact the second liquid; and
a driving unit configured to apply a potential difference across the membrane via the first and second electrodes, the potential difference being such as to promote insertion of a membrane protein into the membrane from the first liquid or the second liquid, wherein:
the driving unit is configured such that a reduction in resistance through the membrane caused by insertion of the membrane protein into the membrane directly causes the driving unit to apply a lower potential difference across the membrane without any logic control of the driving unit.

In a yet further aspect, there is provided an apparatus for controlling insertion of a membrane channel into a membrane, comprising:
  a first bath for holding a first liquid in contact with a first surface of the membrane;
  a second bath for holding a second liquid in contact with a second surface of the membrane, wherein the membrane separates the first and second liquids;
  a first electrode configured to contact the first liquid;
a second electrode configured to contact the second liquid; and
a driving unit configured to apply a potential difference across the membrane via the first and second electrodes to promote insertion of a membrane channel into the membrane from the first liquid or the second liquid, wherein:
the apparatus comprises a membrane voltage reduction unit connected in series with the membrane.

Insertion of a membrane channel is controlled by the intrinsic properties of the membrane voltage reduction unit combined with its position in series with the membrane. The lowering of the potential difference across the membrane is triggered naturally when insertion happens. This is in contrast to the prior art methods wherein lowering of the potential difference is effected by logic control, which can be complex and/or inconvenient.

Insertion of a channel into the membrane typically takes place by adding membrane channels to an aqueous solution in contact with the membrane.

In some embodiments, the apparatus comprises a plurality of membranes, each membrane separating a first liquid from a second liquid. A plurality of the second baths may be provided for containing the second liquid, wherein each second liquid is separated from each other. The second liquids are typically provided in respective wells. The first liquid may also be provided in a respective plurality of wells that are separated from each other. More typically the first liquid is common to all of the membranes of the array and provided in a single chamber. Electrodes may be provided in each of the second liquids and a common electrode provided in the first liquid. In the case of a plurality of first baths, electrodes may also be provided in each of the first and second baths. In this way individual channel recordings may be made for each membrane of the array. Conveniently the channels may be added to the first solution that is common to the plurality of membranes. The apparatus is configured to support a plurality of membranes wherein each membrane is in contact with and separates the first and second liquids. Suitable apparatus designs for a membrane array as well as suitable methods for providing the second solution into the respective wells of the array, for forming the plurality of membranes across the array as well as for adding the membrane channels to the apparatus for insertion into the membranes are disclosed by WO2014064443 the relevant contents of which are herein incorporated by reference. Formation of membranes across the array may be carried out by a step-wise process such as disclosed by WO2014064443. A plurality of the membrane voltage reduction units is provided wherein each membrane voltage reduction unit is connected in series with a respective membrane of the array. The driving unit is configured to apply the driving voltage in parallel across all of the pairs of membrane voltage reduction unit and different membrane.

In an alternative arrangement, the apparatus may comprise first and second baths wherein both baths are common to the array of membranes and wherein each bath contains an electrode. Such arrangements are possible when measuring a voltage change employing an FET wherein the change is voltage is local to a particular channel. In this way and according to some embodiments multiple channels can be provided within a single membrane.

Providing plural membrane voltage reduction units in this manner makes it possible to control insertion of channels in multiple second baths simultaneously while applying the same driving voltage to the multiple second baths. It is thus possible to insert channels in multiple second baths in parallel without generating multiple independent driving voltages, thus saving time and improving yield.

In an embodiment, the membrane voltage reduction unit comprises a current source capable of supplying a constant current through resistances up to a maximum resistance at which resistance the voltage limit is reached. The constant current may be predetermined but alternatively may be set by logic control. In this embodiment the lowering of the potential difference across the membrane is caused by the resistance through the membrane being reduced from a resistance above said maximum resistance to a resistance below said maximum resistance. The inventors have found this implementation to provide particularly advantageous properties. The potential difference across the membrane is reliably lowered immediately on insertion of a channel, and remains at a stable, low value even when the driving voltage continues to be increased to a maximum value.

According to a further aspect, there is provided a method of controlling insertion of a membrane channel into a membrane, comprising:
providing a membrane in contact with and separating first and second liquids on respective first and second sides of the membrane;
using a driving unit to apply a potential difference across the membrane via the first and second electrodes to promote insertion of a membrane channel into the membrane from the first liquid or the second liquid, wherein:
the driving unit comprises a membrane voltage reduction unit connected in series with the membrane;
the driving unit is configured to apply a driving voltage across the membrane voltage reduction unit and the membrane, the driving voltage providing the potential difference across the membrane; and
the membrane voltage reduction unit is configured such that the reduction in resistance through the membrane caused by insertion of the membrane channel intrinsically increases a potential difference across the membrane voltage reduction unit thereby lowering the potential difference across the membrane, wherein the lowering of the potential difference across the membrane is sufficient to prevent or reduce promotion of insertion of a further membrane channel.

According to a yet further aspect, there is provided a method of inserting a membrane protein into a membrane to form a channel in the membrane, comprising:
providing a membrane in contact with and separating first and second liquids on respective first and second sides of the membrane;
using a driving unit to apply a potential difference across the membrane via the first and second electrodes, the potential difference being such as to promote insertion of a membrane protein into the membrane from the first liquid or the second liquid, wherein:
the driving unit is configured such that a reduction in resistance through the membrane caused by insertion of the membrane protein into the membrane directly causes the driving unit to apply a lower potential difference across the membrane without any logic control of the driving unit.

BRIEF DESCRIPTION OF THE DRAWINGS

Embodiments of the invention will now be described, by way of a non-limiting example only, with reference to the accompanying drawings in which corresponding reference symbols indicate corresponding parts, and in which according to some embodiments of the disclosure.

DETAILED DESCRIPTION OF THE INVENTION

This disclosure generally relates to systems and methods for controlling the insertion of a membrane channel into a membrane. In some embodiments, the membrane separates a first liquid from a second liquid. In some embodiments, a driving unit applies a potential difference across the membrane via a first electrode contacting the first liquid and a second electrode contacting the second liquid, to promote insertion of a membrane channel into the membrane from the first liquid or the second liquid. In some embodiments, a membrane voltage reduction unit, connected in series with the membrane, is configured such that a reduction in resistance through the membrane caused by insertion of a membrane channel intrinsically increases a potential difference across the membrane voltage reduction unit, thereby lowering the applied potential difference across the membrane, in some cases sufficiently to prevent or reduce a probability of insertion of a further membrane channel.

Figure 3:
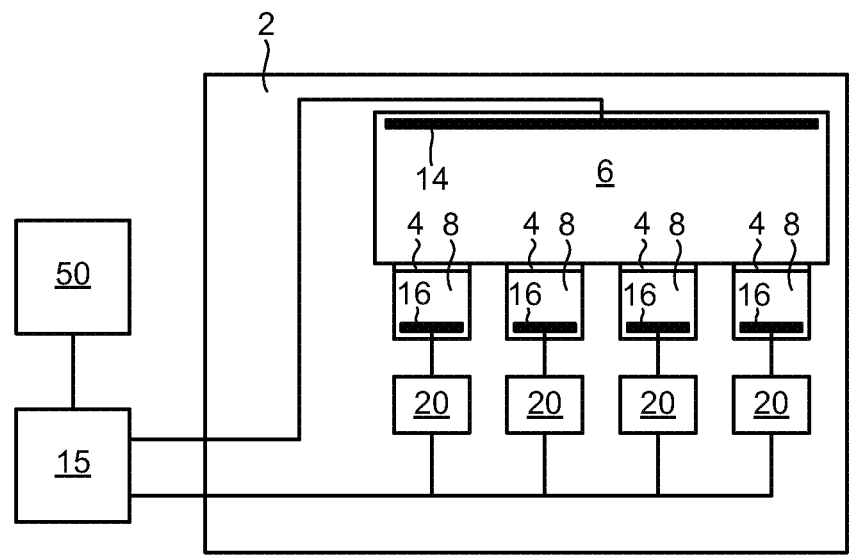
FIG. 3 depicts an apparatus for controlling insertion of a membrane channel into a membrane according to an embodiment.

FIG. 3 depicts an apparatus for controlling insertion of a membrane channel into a membrane 4 according to an embodiment. The apparatus comprises a housing 2 containing a first bath 6. The housing 2 further contains four second baths 8 (also referred to as wells). A different number of second baths 8 may be provided in other embodiments. Each second bath 8 is sealed by a membrane 4. The membrane 4 may be an amphiphilic membrane. The first bath 6 holds a first liquid. The first liquid contacts a first surface of each membrane 4. Each second bath 8 holds a second liquid. The second liquid in each second bath 8 contacts a second surface of the membrane 4 sealing that second bath 8. A first electrode 14 contacts the first liquid. A second electrode 16 contacts each second liquid. Each second bath 8 has its own second electrode 16.

The housing 2 is shown with only a single first bath 6 and four second baths 8 with associated membranes 4. In other embodiments, many more first baths 6 and second baths 8, and corresponding first electrodes 14 and second electrodes 16, may be provided. The number of second baths may be any integer between 1 and 100,000. It may be 100 or more, 1000 or more or 10,000 or more.

The first and second electrodes 14, 16 can be used to control the insertion of the channel, as described below. In certain embodiments, at a later time after the channel has been inserted, the first and second electrodes 14, 16 can also be used to sense molecular entities via their interaction with the channel.

A driving unit 15 is configured to apply a potential difference across the membrane 4 (which may also be referred to as a membrane voltage) via the first and second electrodes 14, 16. The applied membrane voltage can be such as to promote insertion of a membrane channel into the membrane 4 from the first liquid 6 or the second liquid 8. Membrane channels (which may comprise membrane proteins for example) are thus provided in the first liquid or the second liquid or both. The membrane voltage promotes insertion of the membrane channel. As mentioned in the introductory part of the description and without wishing to be bound by theory, it is thought that the voltage assists insertion by stretching and thinning the membrane 4. The voltage at which insertion happens varies from membrane 4 to membrane 4. The driving unit 15 may therefore be configured to increase the membrane voltage progressively until insertion occurs.

The amount of applied potential required for nanopore insertion may vary between membranes of an array. Without wishing to be bound by theory, it is thought that this difference may arise due to a variation in thickness between membranes of the array and influenced by the chemical nature of the membrane and nanopore as well its geometry. The applied voltage is typically stepped in magnitude such as to maximise the chances of single channel insertion. For example if the starting potential is too high, it may promote the insertion of further channels for some membranes which is undesirable whilst the applied potential may not sufficiently high enough for other membranes of the array. Thus it is preferable to start from a low value of potential and move progressively to higher values. The potential may be increased by different methods such as by ramping the potential over time or stepping between values of potential at progressively higher values. The rate of increase may be linear or non-linear. The initial and maximum driving voltages that are chosen will depend upon the nature of the membrane and the membrane channel and can be selected appropriately. As mentioned the potential required to insert a membrane channel has been observed to vary across membranes of the array, despite the fact that the initial membrane solution applied to the array may be the same and the same membrane channels may inserted across membranes of the array. Thus any variation in the required voltage to insert the membrane channels is most probably due to variation of other factors, such as membrane thickness. Thus the parameters for the rate of increase of voltage and/or initial and final potential will be influenced and determined by the process of formation of membranes. By way of example, the initial potential value may be chosen from a value anywhere between 0 mV and 150 mV, such as 50, 75 or 100 mV and the final membrane potential may be chosen from a value anywhere between 200 and 600 mV, such as a 250, 300, 350, 400, 450 or 500 mV. The upper limit of membrane potential will be determined in part by the stability of the membranes. For example, lipid bilayers are not as robust as some synthetic membranes. Similarly, the rate of increase in potential between the initial and final values will also depend upon the nature of the membrane and the membrane channel and can also be selected appropriately. By contrast with the prior art computer controlled method, the rate of increase between initial and final values may be far more rapid as be less than 1 s. The rate of increase between the initial and maximum potential could in principle be of the order of between 10 and 100 ms. In practice, rate of increase will be dependent upon the nature of the membrane and how stable it is when subjected to rapid changes in potential difference applied across it. In the prior art, one might typically employ 1-10 mV steps with 1 to 15 seconds per step wherein the whole process could take tens of minutes. Because the need to wait for a processing unit to detect when insertion has taken place and respond to the detection has been removed in the method and apparatus of the invention, the increase of the driving voltage to a level at which insertion takes place can be made to occur more quickly, thereby improving throughput.

Alternatively a single membrane potential may applied to the plurality of membranes of the array namely wherein the membrane potential is very rapidly or instantaneous stepped from a lower to a higher potential. This method could be used where all membranes are sufficiently alike as to allow a single insertion voltage above a critical voltage to be employed.

Following membrane insertion the voltage is reduced to a level so as to prevent or significantly reduce the chance of further membrane channel insertion. The extent which the potential is lowered will depend upon the nature of the membrane and the membrane channel and a suitable value can be selected as appropriate. The extent to which the potential is lowered could be for example 10, 20, 30, 40, 50, 60 or 70% of the potential required to insert a membrane channel Given that the potential required for channel insertion may vary across an array, the lowering of the potential should be a value below that of the lowest potential required to insert a membrane channel in a membrane. Thus the lowering of the applied potential difference across the membrane to reduce the promotion of insertion of a further membrane channel reduces the probability of insertion of a further membrane channel.

Following insertion of the desired number of membrane channels, for example a single membrane channel in membranes of the array, the excess membrane channels may be removed, for example by removing the first solution and optionally replacing with a further solution without membrane channels. Whilst the membrane channel insertion in the absence of an applied stimulus may not subsequently take place automatically, removal of the excess membrane channels may nonetheless be carried out to remove the possibility of further membrane channel insertion taking place in the absence of an applied stimulus. Furthermore, once channel insertion into a membrane occurs, typically the channel remains within the membrane and does leach out into the first and second solutions.

In some embodiments it is desirable to provide a single membrane channel per membrane 4. It is thus desirable to lower or remove the membrane voltage as soon as insertion of a membrane channel occurs.

Figure 1:
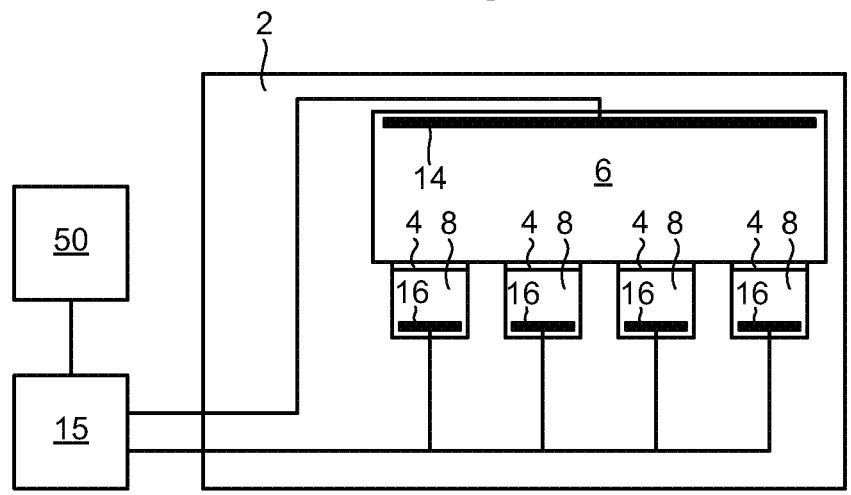
FIG. 1 depicts a prior art apparatus for controlling insertion of a membrane channel into a membrane.

In a prior art arrangement, as depicted schematically in FIG. 1 (where features corresponding to features in FIG. 3 are given corresponding reference signs), this is achieved by computer control of a driving voltage 30 applied between the first electrode 14 and a second electrode 16 using a processing unit 50. The processing unit 50 may comprise any of the known hardware and/or firmware and/or software components that enable computer control to be performed. In this prior art arrangement, the processing unit 50 monitors the electrical characteristics of the electrical circuit formed between the first electrode 14 and the second electrode 16 (i.e. through the first bath 6, membrane 4 and second bath 8), while progressively increasing the driving voltage 30. When insertion of a membrane channel is detected (e.g. via a sudden increase in the current between the first electrode 14 and the second electrode 16), the processing unit 50 immediately decreases the driving voltage 30 applied between the first electrode 14 and the second electrode 16 (typically to zero). This may be done for example by instructing a switching unit (not shown) to disconnect the second electrode 16 of the currently selected second bath 8 and allow it to float or connect the second electrode to ground to ground instead of to a driving voltage 30. The processing unit 50 may then cause the switching unit to simultaneously connect the driving voltage 30 to a different one of the second baths 8 and start progressively increasing the driving voltage 30 applied to the new second bath 8 until insertion of a membrane channel is detected for that second bath, and so on.

In this sense the switch which is controlled by the processing unit fulfils the function of the voltage reduction unit. When it is closed all the driving voltage is across the membrane. When it is open all the voltage is across the switch. The key difference between the prior art arrangement and the invention is that the prior art requires control by a processing unit in order to reduce the applied voltage. The switch would also require a current source to activate the switch (via computer or digital control)

In the example of FIG. 1, the process may be repeated four times in order to insert one membrane channel in each of the four membranes 4.

Figure 2:
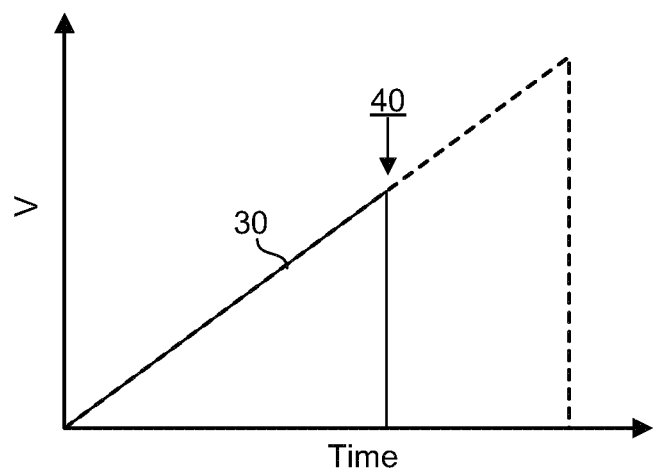
FIG. 2 is a graph depicting driving voltage against time.

By way of example, the variation in the driving voltage 30 for a single insertion event is shown schematically in FIG. 2. The processing unit 50 increases the driving voltage 30 progressively at a constant rate until an insertion is detected. In the example shown, the insertion event happens at arrow 40. The broken line curve shows how the driving voltage 30 would have continued had the insertion not occurred.

Although the approach described above with reference to FIGS. 1 and 2 can prevent or reduce multiple membrane channel insertions in the same membrane, the requirement to repeat the progressive increase of the driving voltage is time consuming and can reduce yield. Furthermore, implementing the computer control is complex and inconvenient.

In an embodiment, of which FIG. 3 is an example, the apparatus further comprises a membrane voltage reduction unit 20 connected in series with the membrane 4. In the particular example of FIG. 3, four membrane voltage reduction units 20 are provided, each connected in series with a corresponding different membrane 4.

The driving unit 15 is configured to apply a driving voltage 30 across the membrane voltage reduction unit 20 and the membrane 4. In the example shown the driving voltage 30 is applied from the first electrode 14 through to a side of the membrane voltage reduction unit 20 opposite to the first electrode 14 (i.e. the voltage increases/falls along an electrical path from the first electrode 14 through the first bath 6, the membrane 4, the second bath 8, the second electrode 16, and the membrane voltage reduction unit 20).

The membrane voltage reduction unit 20 is configured such that a reduction in resistance through the membrane 4 caused by insertion of a membrane channel in the membrane 4 intrinsically (i.e. without any external computer control) increases a potential difference across the membrane voltage reduction unit 20. The increase in the potential difference across the membrane voltage reduction unit 20 lowers the potential difference across the membrane 4. This is because the series circuit from the first electrode 14 to the side of the membrane voltage reduction unit 20 opposite to the first electrode 14 acts as a potential divider. The membrane voltage reduction unit 20 is configured so that the lowering of the potential difference across the membrane 4 is sufficient to prevent or reduce promotion of insertion of a further membrane channel.

Thus, reduction of the applied membrane across the membrane and control over subsequent membrane channel insertion is controlled through intrinsic properties of the membrane voltage reduction unit 20 combined with its position in series with the membrane 4.

The membrane voltage reduction unit is configured such that the lowering of the potential difference across the membrane is triggered without logic control. No logic control is required in order to lower the applied potential across the membrane. Examples of what is meant by logic control are computer, digital or manual control. Use of an FPGA to lower the applied potential would be an example of logic control.

Providing plural membrane voltage reduction units 20, one for each of a corresponding plurality of membranes 4, it is possible to control insertion of channels in multiple second baths simultaneously while applying the same driving voltage 30 to all of the second baths. In comparison with the prior art arrangements of the type discussed above with reference to FIGS. 1 and 2, it is no longer necessary to apply progressive ramps of voltage in a sequential manner (one after the other). Membranes can thus be inserted in parallel, saving time and improving yield. Furthermore, because there is no longer any need to wait for a processing unit 50 to detect when insertion has taken place, the progressive increase of the driving voltage 30 can be made to take place in a shorter time period, further increasing speed. In certain embodiments, the progressive increase in driving voltage 30 may even be dispensed with (by immediately applying a voltage that is above a level at which membrane insertion is expected to occur). As soon as a membrane channel inserts, the membrane voltage will fall to a level that is too low to promote further insertions. This approach simplifies implementation but may increase the risk of multiple channel insertion in the same second bath. The increased risk of multiple channel insertion arises because the initially applied voltage may be significantly higher than is necessary for the insertion.

The embodiment of FIG. 3 is an example in which a plurality of second baths 8 are provided, wherein each second bath 8 supports a different membrane 4. It is not however essential for each second bath 8 to have a different membrane 4. In other embodiments, each second bath 8 may be sealed by a different portion of the same membrane 4 (i.e. such that membrane spans over the entrance to a plurality of different second baths 8). Where plural such second baths 8 are provided, each membrane voltage reduction unit 20 is connected in series with a different membrane (in the case where each second bath 8 is sealed by a different membrane 4) or a different portion of the same membrane 4 (in the case where the membrane 4 spans over the entrance to a plurality of different second baths 8). In embodiments of this type, the driving unit 15 can be configured to apply the driving voltage 30 in parallel across all of the pairs of membrane voltage reduction unit 20 and membrane 4 or across all of the pairs of membrane voltage reduction unit 20 and corresponding different portion of the same membrane 4 (as applicable).

Figure 4:
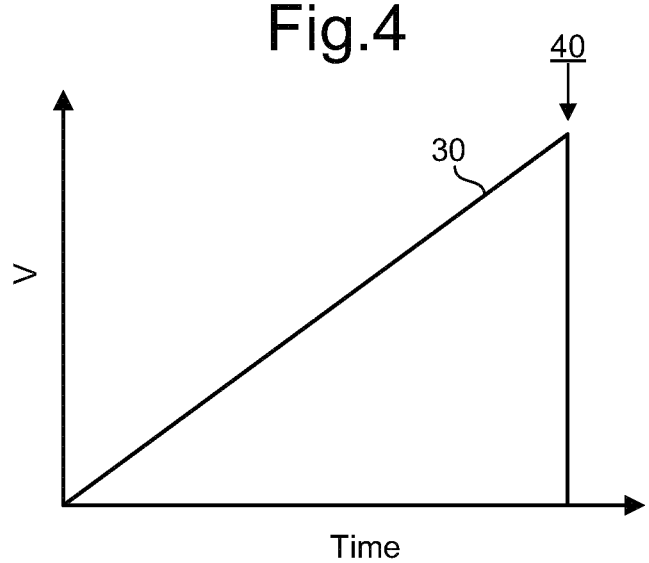
FIG. 4 is a graph depicting driving voltage against time for the simulations of FIGS. 6, 8 and 10.
Figure 5:
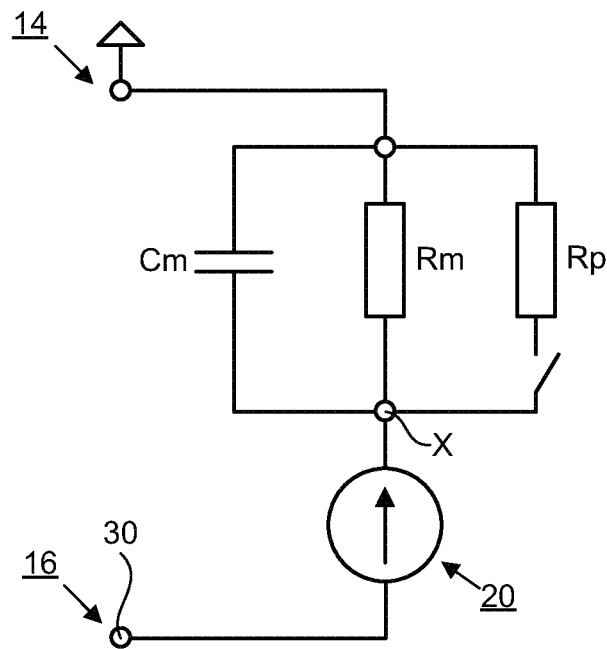
FIG. 5 depicts an equivalent circuit illustrating operation of an embodiment in which a membrane voltage reduction unit comprises a current source.
Figure 6:
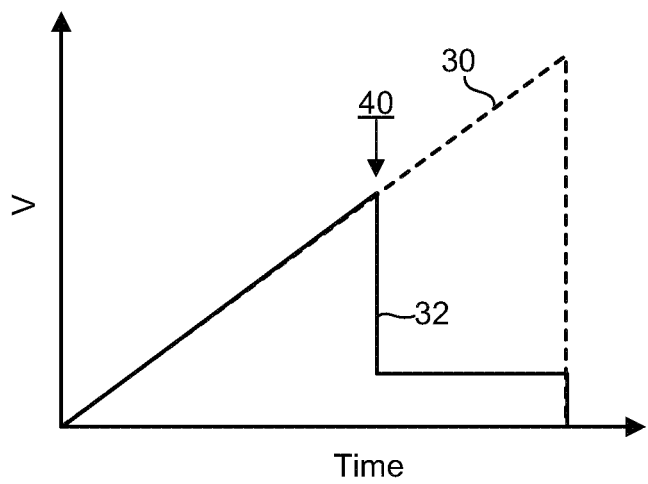
FIG. 6 is a graph showing a simulated variation of membrane voltage with time when the driving voltage of FIG. 4 is applied to the equivalent circuit of FIG. 5.
Figure 7:
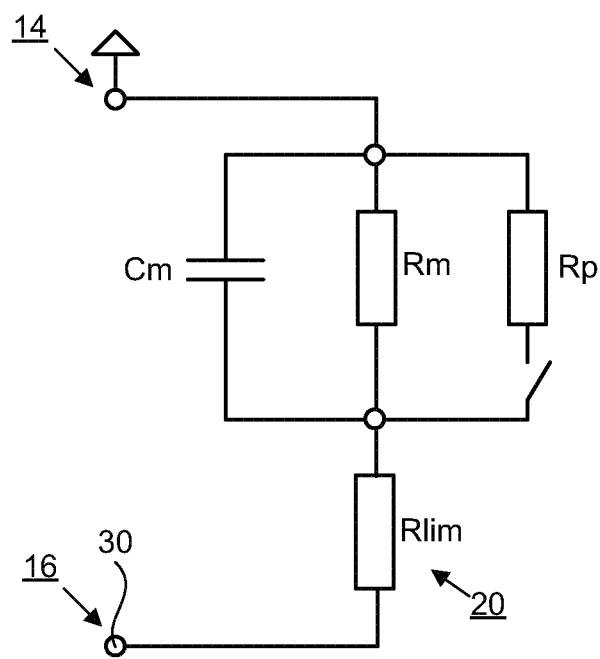
FIG. 7 depicts an equivalent circuit illustrating operation of an embodiment in which a membrane voltage reduction unit comprises a resistive component in series with the membrane.
Figure 8:
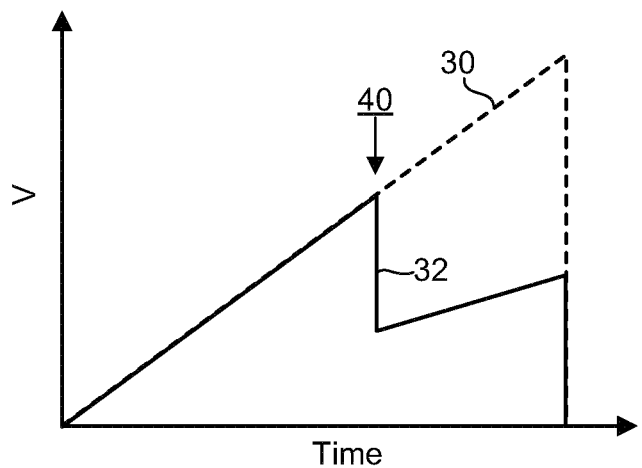
FIG. 8 is a graph showing a simulated variation of membrane voltage with time when the driving voltage of FIG. 4 is applied to the equivalent circuit of FIG. 7.
Figure 9:
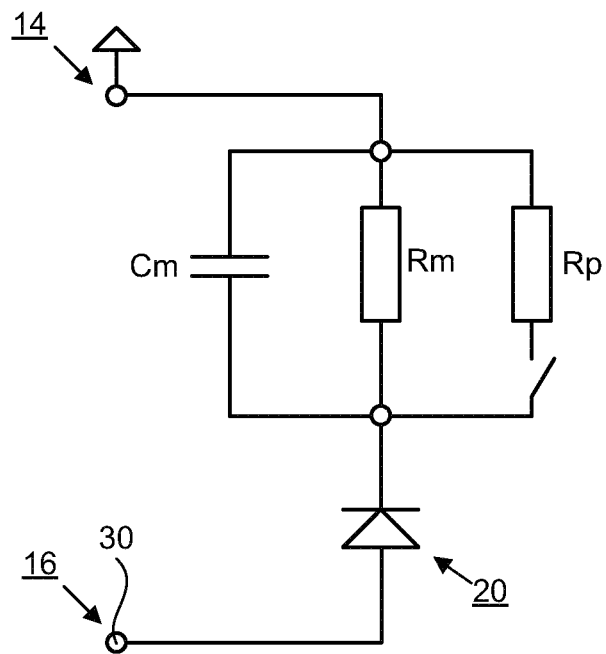
FIG. 9 depicts an equivalent circuit illustrating operation of an embodiment in which a membrane voltage reduction unit comprises a diode in series with the membrane.
Figure 10:
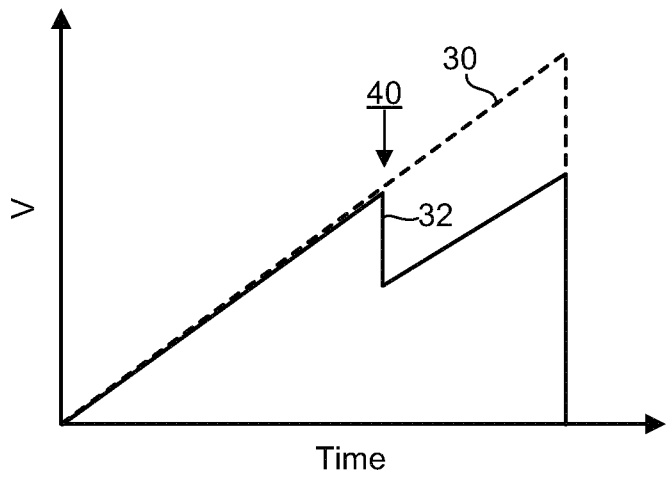
FIG. 10 is a graph showing a simulated variation of membrane voltage with time when the driving voltage of FIG. 4 is applied to the equivalent circuit of FIG. 9.

The membrane voltage reduction unit 20 may be implemented in various ways. Three example implementations are described below with reference to FIGS. 4-10. FIGS. 5, 7 and 9 show equivalent circuits for each of the three implementations. FIGS. 6, 8 and 10 show the results of simulations of how the membrane voltage 32 will vary with time when the progressively increasing driving voltage of FIG. 4 is applied to each of the equivalent circuits of FIGS. 5, 7 and 9. In each case, channel insertion is indicated by arrow 40.

The progressive increase of driving voltage 30 of FIG. 4 can be configured in various different ways. For the simulations shown, the driving voltage 30 was increased from zero to 450 mV. A channel insertion voltage was set to 280 mV. The resistance of the channel (pore) Rp was set to 0.67 Gohm.

In the embodiment of FIGS. 5 and 6, the membrane voltage reduction unit 20 comprises a current source. The current source is capable of supplying a constant current through resistances up to a maximum resistance. Such current sources are known in the art and can be provided in various forms. In this embodiment, the lowering of the potential difference across the membrane is caused by the resistance through the membrane being reduced from a resistance above said maximum resistance to a resistance below said maximum resistance. The behaviour can be understood by referring to the equivalent circuit of FIG. 5. In this circuit, Cm represents a capacitance of an intact membrane 4, Rm represents a resistance of an intact membrane 4, and Rp represents a resistance through an inserted membrane channel A switch is shown in this branch to indicate that the inserted membrane channel will not always be present. Rp is much lower than Rm, so when a membrane channel inserts Rp effectively short-circuits Rm (and Cm). When the switch in the Rp branch is closed (channel inserted), the resistance of the parallel arrangement of Cm, Rm and Rp is dominated by Rp (i.e. is approximately equal to Rp). When the switch in the Rp branch is open (channel not inserted), the resistance of the parallel arrangement of Cm, Rm and Rp is dominated by Rm (i.e. is approximately equal to Rm).

In the present embodiment, the current source is capable of applying the constant current by varying a potential at point X between ground and the driving voltage 30. The first electrode 14 is connected to ground in this embodiment, so the potential difference across the membrane (neglecting the first bath 6 and the second bath 8) is approximately equal to X. The driving voltage 30 is thus the maximum potential difference that the current source can apply to the membrane 4. If the driving voltage 30 is insufficient to cause the predetermined constant current to flow, the current source will drive the voltage at X to as near as possible to X, which is the most the current source can do to try and achieve the predetermined constant current. The current source is configured (by appropriate selection of the predetermined constant current) so that the driving voltage 30 will be insufficient to cause the predetermined constant current to flow when the switch in the Rp branch is open. Thus, Rm is above the maximum resistance through which the current source is capable of driving the constant current. On the other hand, the current source is configured such that Rp is below the maximum resistance. Thus, when insertion happens, the current source is now capable of driving the constant current through the membrane 4 (mostly through the newly inserted channel). Furthermore, this can be achieved by applying a voltage at X that is much lower than the driving voltage 30, thereby lowering the potential difference across the membrane 4 so as to prevent or reduce insertion of a further membrane channel. This functionality is achieved using a standard current source acting in a standard way. No computer control of the current source is necessary for the current source to respond as desired to insertion of a channel. Suitable current sources can be implemented easily in silicon, thereby facilitating manufacture.

FIG. 6 illustrates the type of behaviour that can be obtained using the embodiment of FIG. 5. The membrane voltage 32 falls immediately on insertion of a channel (arrow 40) and remains low and stable even while the driving voltage 30 continues to ramp up. Even when the driving voltage 30 has reach its maximum value, the membrane voltage 32 has barely changed since the insertion at point 40. The risk of the membrane voltage 32 promoting any further channel insertion is thus very low. In the particular simulation shown, the current source was set to provide 100 pA, so the membrane voltage 32 after insertion was about 67 mV (100 pA*0.67 Gohm).

In the embodiment of FIGS. 7 and 8, the membrane voltage reduction unit 20 comprises a resistive component in series with the membrane 4. The resistance Rlim of the resistive component is selected so that when the Rp branch is open (channel not inserted), the membrane voltage is a sufficiently large proportion of the driving voltage 30 that channel insertion can be promoted effectively, but that when the Rp branch is closed (channel inserted), the resistance Rlim is sufficiently large that the membrane voltage falls to a level that is low enough to prevent or reduce promotion of insertion of a further membrane channel. In general Rlim will need to be high, typically above about 1 Gohm.

FIG. 8 illustrates the type of behaviour that can be obtained using the embodiment of FIG. 7. As can be seen, the membrane voltage 32 falls immediately on insertion of a channel and remains relatively low (although increasing slowly) while the driving voltage 30 continues to ramp up. Even when the driving voltage 30 has reached its maximum value, however, the membrane voltage 32 has not risen to a level that would significantly promote channel insertion.

In the embodiment of FIGS. 9 and 10, the membrane voltage reduction unit 20 comprises a diode in series with the membrane 4. The properties of the diode are selected so that when the Rp branch is open (channel not inserted), the membrane voltage is a sufficiently large proportion of the driving voltage 30 that channel insertion can be promoted effectively, but that when the Rp branch is closed (channel inserted), the membrane voltage falls sufficiently that the membrane voltage falls to a level that is low enough to prevent or reduce promotion of insertion of a further membrane channel.

FIG. 10 illustrates the type of behaviour that can be obtained using the embodiment of FIG. 9. The membrane voltage 32 falls immediately on insertion of a channel and remains relatively low for a significant period of time while the driving voltage 30 continues to ramp up. For the particular diode characteristics used in this simulation, when the driving voltage 30 has reached its maximum value, the membrane voltage 32 has risen to a level comparable with the voltage at which channel insertion took place (point 40). The risk of further membrane insertion could however be reduced in this embodiment by reducing the maximum value of the driving voltage 30. Reducing the maximum value of the driving voltage 30 may reduce the proportion of the membranes that have a channel successfully inserted, but would also reduce the proportion of membranes in which more than one channel is inserted. Although the behaviour of FIG. 10 is apparently less desirable than the behaviour of FIGS. 6 and 8, the embodiment of FIG. 9 may nevertheless be desirable in certain circumstances due to ease of manufacture. Diodes are readily available, can be implemented in compact form (they are easily built into silicon or assembled on a PCB), and may even be present in circuitry that is intended for other purposes but which can be adapted or exploited for use in the present context. The embodiment of FIGS. 9 and 10 may be easier to implement than the embodiment of FIGS. 7 and 8 because it is generally easier to provide a suitable diode in silicon or on a PCB than it is to provide the very high resistances needed for the resistor Rlim of FIG. 7.

As shown in the embodiments of FIGS. 4-10, the driving unit 15 may be configured such that the driving voltage 30 progressively increases up to a predetermined maximum driving voltage. This behaviour could be controlled by hardware or control could be applied by a processing unit 50 (as shown in FIG. 3). As described above, however, in the case where a processing unit 50 is involved, the processing unit 50 is not required to trigger lowering of the potential difference across the membrane when insertion of a channel occurs because of the intrinsic properties of the membrane voltage reduction unit 20.

In an embodiment, the driving unit 15 is configured such that the driving voltage 30 progressively increases to the predetermined maximum driving voltage in less than 5 sAs mentioned above, this ramping can be applied more quickly than in prior art arrangements because it is not necessary to provide time for computer control. The intrinsic properties of the membrane voltage reduction unit 20 allow the unit to respond more quickly to a channel insertion than a computer typically could (without providing excessively expensive hardware).

As mentioned in the introductory part of the description, an inserted membrane channel (or nanopore) can be used to perform sensing. Further exemplary details are given below.

In an embodiment, the nanopore is used in a molecular entity sensing apparatus to determine a characteristic of an analyte. The analyte to be determined may be polymeric such as an amino acid, peptide, polypeptide, a protein or a polynucleotide. The polynucleotide may comprise any combination of any nucleotides. The nucleotides can be naturally occurring or artificial. One or more nucleotides in the polynucleotide can be oxidized or methylated. The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid known in the art. The analyte to be determined may be an amptamer. The molecular entity may be caused to translocate the pore and the interactions between the molecular entity and the pore measured.

Translocation of the analyte through the channel may be assisted by a motor protein such as a polynucleotide handling enzyme. Preferred enzymes are polymerases, exonucleases, helicases and topoisomerases, such as gyrases. Any helicase may be used in the invention. The helicase may be or be derived from a He1308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561). Alternatively translocation of the analyte through the pore may also be assisted by voltage control, such as disclosed by International Patent Application PCT/US2008/004467.

The characteristic to be determined may be a sequence characteristic of the polymer. Determination of a sequence characteristic may be carried out by methods disclosed by International Patent Applications PCT/GB2012/052343 and PCT/GB2013/050381.

The membrane channel may be a nanopore which may be a naturally occurring pore, a mutated pore derived from a naturally occurring pore or a synthetic a pore. The membrane channel will have channel width typically from between 0.5 nm and 25 nm and may vary in channel width along its length. The pore may be homo-oligomeric, namely, derived from identical monomers. The pore may be hetero-oligomeric, namely where at least one monomer differs from the others. Transmembrane protein pores for use in accordance with the invention can be derived from β-barrel pores or α-helix bundle pores. Suitable pores include, but are not limited to, α-hemolysin, anthrax toxin and leukocidins, outer membrane proteins/porins of bacteria, such as *Mycobacterium smegmatis* porin (Msp), for example MspA, MspB, MspC or MspD, CsgG, outer membrane porin F (OmpF), outer membrane porin G (OmpG), outer membrane phospholipase A and *Neisseria* autotransporter lipoprotein (NalP) and other pores, such as lysenin, WZA and ClyA toxin, Sp1, lysenin or FraC.

Suitable pores derived from CsgG are disclosed in WO 2016/034591. Suitable pores derived from lysenin are disclosed in WO 2013/153359. The pore may be a DNA origami pore, as described by Langecker et al., Science, 2012; 338: 932-936, hereby incorporated by reference.

The membrane may be amphiphilic (also referred to as an amphiphilic membrane). An amphiphilic membrane is one formed from amphiphilic molecules, such as phospholipids, which have both hydrophilic and lipophilic properties. The amphiphilic layer may be a monolayer or a bilayer. The amphiphilic layer may be a co-block polymer such as disclosed by, Gonzalez-Perez et al., Langmuir, 2009, 25, 10447-10450, and U.S. Pat. No. 6,723,814, both hereby incorporated by reference. The polymer may be a PMOXA-PDMS-PMOXA triblock copolymer.

Measurement methods may include measuring of a current passing through the pore as the analyte moves with respect to the pore. Suitable conditions for measuring ionic currents through transmembrane channel pores are known in the art. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

Alternatively the measurement may be a fluorescence measurement indicative of ion flow through the channel such as disclosed by Heron et al, J. Am. Chem. Soc., 2009, 131 (5), 1652-1653 or measurement of a voltage across the membrane using a FET.

The methods are typically carried out in the presence of any charge carriers, such as metal salts, for example alkali metal salt, halide salts, for example chloride salts, such as alkali metal chloride salt. The liquid is typically aqueous and contains ions. Potassium chloride (KCl), sodium chloride (NaCl), caesium chloride (CsCl) or a mixture of potassium ferrocyanide and potassium ferricyanide may be used. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed below, the buffer is present in the aqueous solution in the chamber. Any buffer may be used. Typically, the buffer is phosphate buffer.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The features defined in the claims or the disclosure may be used together in any combination.

The invention claimed is:

1. An apparatus for controlling insertion of a membrane channel into a membrane, comprising:
   a first bath for holding a first liquid in contact with a first surface of the membrane;
   a second bath for holding a second liquid in contact with a second surface of the membrane, wherein the membrane separates the first and second liquids;
   a first electrode configured to contact the first liquid;
   a second electrode configured to contact the second liquid; and
   a driving unit configured to apply a potential difference across the membrane via the first and second electrodes to promote insertion of a membrane channel into the membrane from the first liquid or the second liquid, wherein:

the apparatus comprises a membrane voltage reduction unit connected in series with the membrane;

the driving unit is configured to apply a driving voltage across the membrane voltage reduction unit and the membrane, the driving voltage providing the potential difference across the membrane; and the membrane voltage reduction unit is configured such that a reduction in resistance through the membrane caused by insertion of a membrane channel increases a potential difference across the membrane voltage reduction unit thereby lowering the potential difference across the membrane, wherein the lowering of the potential difference across the membrane is sufficient to prevent or reduce promotion of insertion of a further membrane channel.

2. The apparatus of claim 1, wherein the membrane voltage reduction unit is configured such that the lowering of the potential difference across the membrane is triggered without logic control.

3. The apparatus of claim 1, wherein:
the membrane voltage reduction unit comprises a current source configured to supply a constant current through resistances up to a maximum resistance; and
the lowering of the potential difference across the membrane is caused by the resistance through the membrane being reduced from a resistance above said maximum resistance to a resistance below said maximum resistance.

4. The apparatus of claim 1, wherein:
the membrane voltage reduction unit comprises a resistive component in series with the membrane, wherein the resistance of the resistive component is selected to ensure that the lowering of the potential difference across the membrane is sufficient to prevent or reduce promotion of insertion of a further membrane channel, while also allowing the potential difference across the membrane to be sufficiently high prior to insertion to promote insertion of the membrane channel prior to insertion.

5. The apparatus of claim 1, wherein:
the membrane voltage reduction unit comprises a diode in series with the membrane, wherein the diode is configured such that the lowering of the potential difference across the membrane is sufficient to prevent or reduce promotion of insertion of a further membrane channel, while also allowing the potential difference across the membrane to be sufficiently high prior to insertion to promote insertion of the membrane channel prior to insertion.

6. The apparatus of claim 1, wherein the driving voltage is increased from a minimum driving voltage to a predetermined maximum driving voltage.

7. The apparatus of claim 6, wherein the increase in driving voltage from a minimum to a maximum value is completed in less than 1 s.

8. The apparatus of claim 1, wherein:
a plurality of the second baths are provided, each second bath being configured to support a different membrane;
a plurality of the membrane voltage reduction units are provided, each membrane voltage reduction unit being connected in series with a different membrane or a different portion of the same membrane; and
the driving unit is configured to apply the driving voltage in parallel across all of the pairs of membrane voltage reduction unit and different membrane or across all of the pairs of membrane voltage reduction unit and different portion of the same membrane.

9. The apparatus of claim 1, wherein the membrane comprises an amphiphilic membrane.

10. A method of controlling insertion of a membrane channel into a membrane, comprising:
providing a membrane in contact with and separating first and second liquids on respective first and second sides of the membrane;
using a driving unit to apply a potential difference across the membrane via first and second electrodes to promote insertion of a membrane channel into the membrane from the first liquid or the second liquid, wherein:
the driving unit comprises a membrane voltage reduction unit connected in series with the membrane;
the driving unit is configured to apply a driving voltage across the membrane voltage reduction unit and the membrane, the driving voltage providing the potential difference across the membrane; and
the membrane voltage reduction unit is configured such that a reduction in resistance through the membrane caused by insertion of the membrane channel increases a potential difference across the membrane voltage reduction unit thereby lowering the potential difference across the membrane, wherein the lowering of the potential difference across the membrane is sufficient to prevent or reduce promotion of insertion of a further membrane channel.

11. The method of claim 10, wherein the membrane voltage reduction unit is configured such that the lowering of the potential difference across the membrane is triggered without computer control.

12. The method of claim 10, wherein:
the membrane voltage reduction unit comprises a current source capable of supplying a predetermined constant current through resistances up to a maximum resistance; and
the lowering of the potential difference across the membrane is caused by the resistance through the membrane being reduced from a resistance above said maximum resistance to a resistance below said maximum resistance.

13. The method of claim 10, wherein:
the membrane voltage reduction unit comprises a resistive component in series with the membrane, wherein the resistance of the resistive component is selected to ensure that the lowering of the potential difference across the membrane is sufficient to prevent or reduce promotion of insertion of a further membrane channel, while also allowing the potential difference across the membrane to be sufficiently high prior to insertion to promote insertion of the membrane channel prior to insertion.

14. The method of claim 10, wherein:
the membrane voltage reduction unit comprises a diode in series with the membrane, wherein the diode is configured such that the lowering of the potential difference across the membrane is sufficient to prevent or reduce promotion of insertion of a further membrane channel, while also allowing the potential difference across the membrane to be sufficiently high prior to insertion to promote insertion of the membrane channel prior to insertion.

15. The method of claim 10, wherein the driving voltage is progressively increased from zero voltage or a minimum driving voltage to a predetermined maximum driving voltage.

16. The method of claim 15, wherein the progressive increase is completed in less than 5 s.

17. The method of claim 10, wherein:
- a plurality of the second baths are provided, each second bath being configured to support a different membrane or a different portion of the same membrane;
- a plurality of the membrane voltage reduction units are provided, each membrane voltage reduction unit being connected in series with a different membrane or a different portion of the same membrane; and
- the driving unit is configured to apply the driving voltage in parallel across all of the pairs of membrane voltage reduction unit and different membrane or across all of the pairs of membrane voltage reduction unit and different portion of the same membrane.

18. The method of claim 10, wherein the membrane comprises an amphiphilic membrane.

\* \* \* \* \*